United States Patent [19]

Schrenker et al.

[11] 4,374,656

[45] Feb. 22, 1983

[54] APPARATUS FOR SOLVENT DEGASSING AND SOLVENT SUPPLY IN LIQUID CHROMATOGRAPHS

[75] Inventors: Helge Schrenker, Karlsruhe; Peter Hupe, Baden-Baden, both of Fed. Rep. of Germany

[73] Assignee: Hewlett-Packard GmbH, Boeblingen, Fed. Rep. of Germany

[21] Appl. No.: 276,848

[22] Filed: Jun. 24, 1981

[30] Foreign Application Priority Data

Jun. 23, 1980 [DE] Fed. Rep. of Germany ....... 3023383

[51] Int. Cl.³ .......................................... B01D 15/08
[52] U.S. Cl. .................................... 55/170; 55/190; 55/196; 55/386
[58] Field of Search ................ 55/43, 44, 53, 67, 170, 55/164, 189, 190, 196, 386, 197

[56] References Cited

U.S. PATENT DOCUMENTS

| | | | |
|---|---|---|---|
| 3,853,500 | 12/1974 | Gassmann et al. | 55/164 X |
| 3,985,626 | 10/1976 | Klein | 55/164 X |
| 4,133,767 | 1/1979 | Bakalyar | 55/53 X |

*Primary Examiner*—John Adee
*Attorney, Agent, or Firm*—Stephen P. Fox; Douglas A. Kundrat

[57] ABSTRACT

An apparatus for solvent degassing and solvent supply in a liquid chromatograph comprises at least one solvent storage vessel, the volume of which is partly filled with liquid solvent while the remaining volume forms a vapor volume. A helium source is connected to said vapor volume for avoiding re-absorption of air by the solvent. A vacuum pump is connected to said vapor volume via a suction line, and a solvent source is connected to said vapor volume via a supply line. A pore filter terminates said supply line within said vapor volume.

5 Claims, 3 Drawing Figures

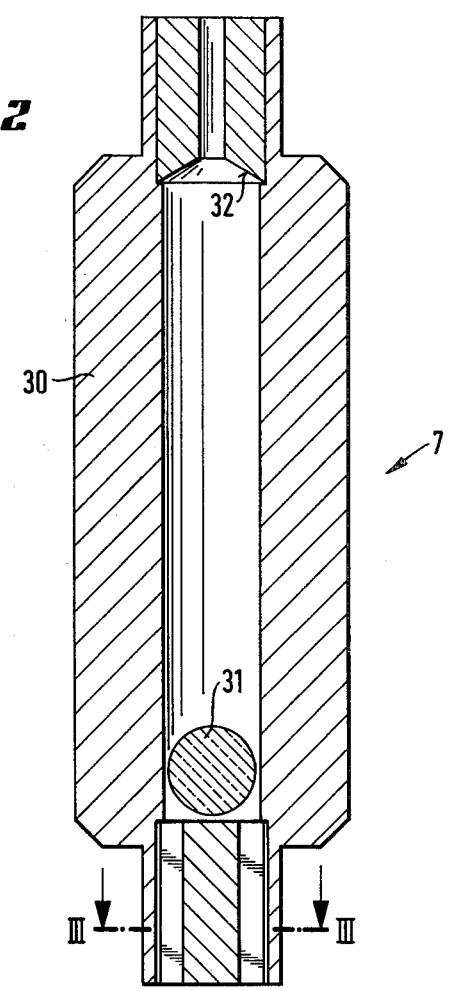
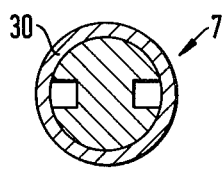

APPARATUS FOR SOLVENT DEGASSING AND SOLVENT SUPPLY IN LIQUID CHROMATOGRAPHS

BACKGROUND OF THE INVENTION

Solvents used as mobile phase in a liquid chromatograph are in their original state usually saturated with air under atmospheric pressure. This may lead to several faults during operation of the chromatograph, e.g., air bubbles may be generated in the region of the suction valves of the solvent pump, causing flow instabilities. Particularly, this occurs when generating solvent gradients, i.e., time dependent controlled variation of the composition ratio of two or more solvents. In order to generate such gradients, two or more solvents, such as water and methanol are mixed before entering the suction valve of the pump. Often the amount of air maximally soluble in the mixture is lower than the sum of the amounts of air maximally soluble in the single mixture components. This causes degassing during the mixing procedure. Additionally, the air dissolved in the solvents can cause errors in the output signals of the sample detectors, either by generating air bubbles in the small volume detector cells, or by affecting the physical or chemical effect on which the detection is based. The above-described problems are discussed in "CZ-Chemietechnik" 1(1972) pgs. 73–78, as well as in A. Zlatkis (editor): "Advances in Chromatography", Houston, Texas, 1978, pages 277–293.

In order to avoid these problems several techniques for solvent degassing have already been proposed and practically used. For example, from Hewlett-Packard Technical Information Bulletin April, 1973, entitled "High-Speed Liquid Chromatograph Model 1010A" it is known to heat and simultaneously to stir the solvent in a closed vessel which is evacuated by a vacuum pump connected to it. However, since most solvents are inflammable, sufficiently safe heating devices require an expensive design.

Another prior art method is an ultrasonics treatment of the solvent, such as described in "Analytical Chemistry", Volume 46, No. 9, August 1974, pgs. 1365–1366. However, this is still more expensive than the above-described solvent heating technique. Moreover, comparison of measurements has shown that it is less effective.

Yet another known method is to introduce a helium stream into the solvent (see e.g. Spectra-Physics Product Bulletin B005 April, 1979, entitled "AP8000 High-Performance Liquid Chromatograph"). By this treatment the dissolved air is "expelled" and instead of the air, helium is dissolved in the solvent. This is per se an effective method requiring only simple devices. However, since the saturation of the solvent with dissolved helium occurs under atmospheric pressure and the saturation solubility is proportional to the static pressure within the solvent, gas bubble generation may occur in system regions on the suction side of the pump, such as in valves or tubes having lower than atmospheric pressure.

SUMMARY OF THE INVENTION

It is an object of the present invention to provide an apparatus for solvent degassing which is simple and inexpensive, effectively avoids gas bubble generation and is capable of automatically supplying the solvent vessels with fresh solvent.

According to a preferred embodiment of the invention, there is provided at least one solvent storage vessel, the volume of which is partly filled with liquid solvent while the remaining volume forms a vapor volume. A helium source is connected to said vapor volume avoiding reabsorption of air by the solvent. A vacuum pump is connected to said vapor volume via a suction line, and a solvent source is connected to said vapor volume by a pore filter. This filter is of such shape and size that a sufficiently quick degassing is achieved by the common effect of short diffusion paths and high partial pressure difference between liquid film and vapor volume.

The apparatus according to the invention not only avoids gas bubbles but has also the advantage that the solvent storage vessels in the liquid chromatograph are automatically refilled from the supply vessels. Thus, a manual refilling of the partly inflammable and toxic solvents is avoided. Moreover, the volume of the storage vessels mounted within the liquid chromatograph can be kept small. This is an advantageous contribution to job safety.

BRIEF DESCRIPTION OF THE DRAWINGS

FIG. 2 is a detailed representation of the liquid trap contained in the apparatus according to FIG. 1.

FIG. 3 is a cutaway view, along the line III—III, of the liquid trap depicted in FIG. 2.

DESCRIPTION OF THE PREFERRED EMBODIMENT

Figure 1:
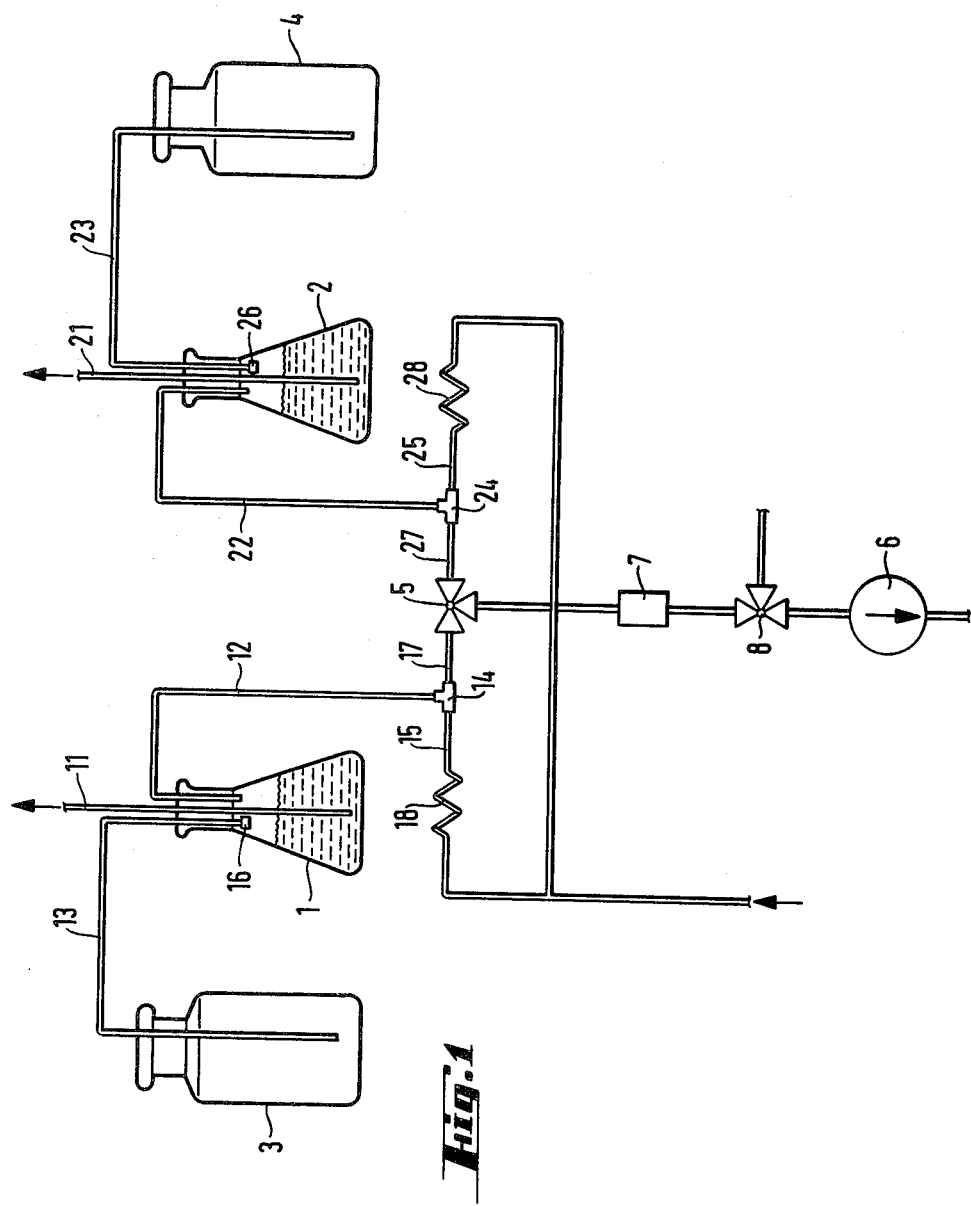
FIG. 1 is a schematic representation of an apparatus for solvent degassing and automatic solvent supply in a liquid chromatograph according to the present invention.

In FIG. 1 reference numerals 1 and 2 designate storage vessels for two different solvents within a liquid chromatograph. Storage vessels 1 and 2 are sealed by screw caps (not shown) which provide gas tight passages for each of the three pipes 11, 12, 13, and the three pipes 21, 22, and 23. Pipes 11 and 21 immerse within storage vessels 1 and 2 into the solvent and lead as suction lines to the solvent pump system of the liquid chromatograph. Pipes 12 and 22 branch in tees 14 and 24, respectively. Via branch pipes 15 and 25, respectively, emerging from tees 14 and 24, and via restriction capillaries 18 and 28, respectively, a helium stream of about 50 ml/min is continuously supplied to the vapor volume of the respective storage vessel. The pressure of the helium source (not shown) is approximately 2 to 3 Bar.

Branch pipes 17 and 27 connect tees 14 and 24, respectively, to two inputs of a three-way valve 5, the output of which is connected via a liquid trap 7 and another three-way valve 8 to a vacuum pump 6. Vacuum pump 6 is preferably a membrane pump with a final vacuum of about 200 millibar.

Pipes 13 and 23 lead to solvent supply vessels 3 and 4 outside the liquid chromatograph, which vessels are preferably the original supply vessels of the solvent manufacturers. Within storage vessels 1 and 2 pipes 13 and 23 are terminated by cylinder shaped filters 16 and 26, respectively. Filters 16 and 26 are preferably frits of stainless steel with an average pore diameter of about 5 $\mu$m and a cylinder surface of about 10 cm$^2$. With vacuum pump 6 in operation, the vapor volume of the storage vessel selected by three-way valve 5 is evacuated, and via filter 16 and 26 fresh solvent is sucked in. The flow resistances of pipes 13 and 23, respectively, and filters 16 and 26, respectively, are matched to the suction power of vacuum pump 6 in such a manner that about 100 ml/min solvent are transmitted and degassed if the viscosity of the solvent is $10^{-3}$ Pas.

Degassing is provided by the vacuum over the filter surface where the solvent emerges slowly and forms a thin film. By means of the vacuum, the partial pressure difference between solvent and vapor volume is increased (as is the diffusion velocity of the dissolved gasses) while the development of the thin liquid film shortens the diffusion paths of the gas molecules in the solvent. Both features commonly provide a quick separation of dissolved gas and solvent. The degree of degassing can be influenced within certain limits by varying the hydrodynamic resistance of pipes 13 and 23, respectively. With vacuum pump 6 not in operation, which is typically the case during most of the operation time of the liquid chromatograph, the vapor volumes of storage vessels 1 and 2 are filled with helium causing a slow replacement of still remaining amounts of air by helium. Via pipes 13 and 23, helium can also flow into solvent supply vessels 3 and 4 where it can cause a pre-degassing. Additionally, solvent remaining in pipes 13 and 23 is expelled so that no further solvent can flow into storage vessels 1 and 2.

The object of three-way valve 8 is to vent the storage vessel selected by three-way valve 5 immediately after vacuum pump 6 stops. This causes an immediate interruption of solvent supply. If vacuum pump 6 is a membrane pump, three-way valve 8 may be omitted, since after stop of the membrane pump pressure balance automatically occurs.

Switching of three-way valves 5 and 8 and starting and stopping of vacuum pump 6 can be manually performed as required. Also, automatic switching is possible by means of level switches in storage vessels 1 and 2. Such level switches would be actuated by predetermined minimum and maximum liquid levels.

The object of the liquid trap 7 is to avoid aspiration of solvent by vacuum pump 6 if the liquid level in the storage vessels 1 and 2, respectively is erroneously too high. FIG. 2 shows this liquid trap in detail.

Referring now to FIG. 2, there is shown a vertically positioned hollow cylinder 30 through which gas flows from bottom to top. Hollow cylinder 30 contains in its inner volume a movable ruby ball 31. The annular slit (about 0.15 mm) between ball 31 and inner cylinder surface is selected such that ball 31 remains at the bottom of the cylinder 30 as long as gas flows through it from the bottom to the top. However, if a liquid enters cylinder 30, ball 31 is driven by the liquid to the top of cylinder 30 where a valve seat 32 is provided. This valve seat 32 is then tightly closed by ball 31.

The apparatus described above may be extended to three or more storage vessels if three-way valve 5 is replaced by a four-way valve or a multi-way valve.

What is claimed is:

1. An apparatus for solvent degassing and solvent supply in a liquid chromatograph comprising:
    at least one solvent storage vessel partly filled with liquid solvent, the remaining volume in said vessel forming a vapor volume;
    means connecting a helium source to said vapor volume for avoiding re-absorption of air by the solvent;
    a vacuum pump connected to said vapor volume via a suction line;
    a solvent source connected to said vapor volume via a supply line; and
    a pore filter terminating the supply line for said solvent source within said vapor volume.

2. An apparatus according to claim 1, wherein the helium source is continuously connected to the vapor volume via a flow resistance.

3. An apparatus according to claim 1, wherein a vent is provided for the vapor volume.

4. An apparatus according to claim 1, wherein a liquid trap is provided between the vapor volume and the vacuum pump.

5. An apparatus according to claim 4, wherein the liquid trap comprises a non-return valve closing in the direction from the vapor volume to the vacuum pump, said non-return valve having a valve housing with a valve seat and a movable valve element, said movable valve element forming with said valve housing a slit within the flow path, said valve being closed when said movable valve element is forced against said valve seat by liquid flow, while remaining open in response to gas flow only.

* * * * *